United States Patent [19]
Ong et al.

[11] Patent Number: 6,158,433
[45] Date of Patent: Dec. 12, 2000

[54] SOFTWARE FOR FINITE STATE MACHINE DRIVEN POSITIVE PRESSURE VENTILATOR CONTROL SYSTEM

[75] Inventors: Raymond Y. Ong; Richard H. Hearn, both of Yorba Linda, Calif.

[73] Assignee: Sechrist Industries, Inc., Anaheim, Calif.

[21] Appl. No.: 09/187,268

[22] Filed: Nov. 6, 1998

[51] Int. Cl.[7] .................................................. A61M 16/00
[52] U.S. Cl. .............................. 128/204.21; 128/204.23; 128/204.18
[58] Field of Search ..................... 128/204.21, 204.23, 128/200.14, 204.18

[56] References Cited

U.S. PATENT DOCUMENTS

| | | |
|---|---|---|
| 5,293,875 | 3/1994 | Stone ........................................ 128/719 |
| 5,357,971 | 10/1994 | Sheehan et al. ......................... 128/719 |
| 5,390,666 | 2/1995 | Kimm et al. . |
| 5,513,631 | 5/1996 | McWilliams . |
| 5,542,410 | 8/1996 | Goodman et al. .................. 128/200.14 |
| 5,542,415 | 8/1996 | Brody . |
| 5,605,158 | 2/1997 | Snell ....................................... 128/696 |
| 5,660,171 | 8/1997 | Kimm et al. . |
| 5,699,357 | 12/1997 | Carvey .................................... 370/346 |

*Primary Examiner*—John G. Weiss
*Assistant Examiner*—Virendra K Srivastava
*Attorney, Agent, or Firm*—Oppenheimer Wolff & Donnelly LLP

[57] ABSTRACT

An improved software control system for a positive pressure ventilator that implements the controller that regulates the ventilator solenoid as a finite state machine. The use of a state machine implementation provides multiple degrees of freedom to the designer and provides for a modular, fail safe design.

36 Claims, 5 Drawing Sheets

SOFTWARE FOR FINITE STATE MACHINE DRIVEN POSITIVE PRESSURE VENTILATOR CONTROL SYSTEM

BACKGROUND OF THE INVENTION

1. Field of Invention

The present invention relates generally to positive pressure ventilators, particularly infant ventilators.

SUMMARY OF THE INVENTION

Historically, ventilators have been designed to be operated in a limited number of modes, with limited degrees of freedom for designers to update the ventilators to be more feature rich and user friendly. Accordingly, an aspect of the present invention is to provide for a software controlled, interrupt driven, finite-state machine driven infant ventilator system that gives a designer more degrees of freedom in designing ventilators and provides for a plurality of improved features, such as providing for a safe, modular design.

Broadly, a state machine, also called a finite state machine, is defined as a computing device designed with the operational states required to solve a specific problem. The circuits are minimized, specialized and optimized for the application in question. For example, chips in audio, video and imaging controllers are often designed as state machines, because they can provide faster performance at lower cost than a general-purpose CPU.

Traditionally, such finite state machines were hardwired, not programmable, or, if programmable, were programmed in a low-level assembly language. Such a design approach is not unreasonable, as it does not compromise safety, since it is known in the art that the higher the level of language, the more likely software errors will be latent in the software. The cost of having a hardwired or hard coded system, however, is that it is inflexible to future design changes and has less degrees of freedom for designers to rapidly implement and change features in response to market conditions.

The present invention discloses a finite state machine implementation of a software controlled, interrupt driven controller (control microprocessor) in an infant ventilator that uses a higher level language, such as C or C++, to implement the finite state machine design, that gives multiple operating modes and multiple degrees of freedom to a designer, but at the same time has numerous fail-safe modes and safety features that make the ventilator as safe or safer than more traditional designs.

The above described and many other features and attendant advantages of the present invention will become apparent from a consideration of the following detailed description when considered in conjunction with the accompanying drawings.

BRIEF DESCRIPTION OF THE DRAWINGS

Detailed description of preferred embodiments of the invention will be made with reference to the accompanying drawings.

DETAILED DESCRIPTION OF THE PREFERRED EMBODIMENTS

Disclosed herein is a detailed description of a best presently known mode of carrying out the invention. This description is not to be taken in a limiting sense, but is made merely for the purpose of illustrating the general principles of the invention.

Figure 1:
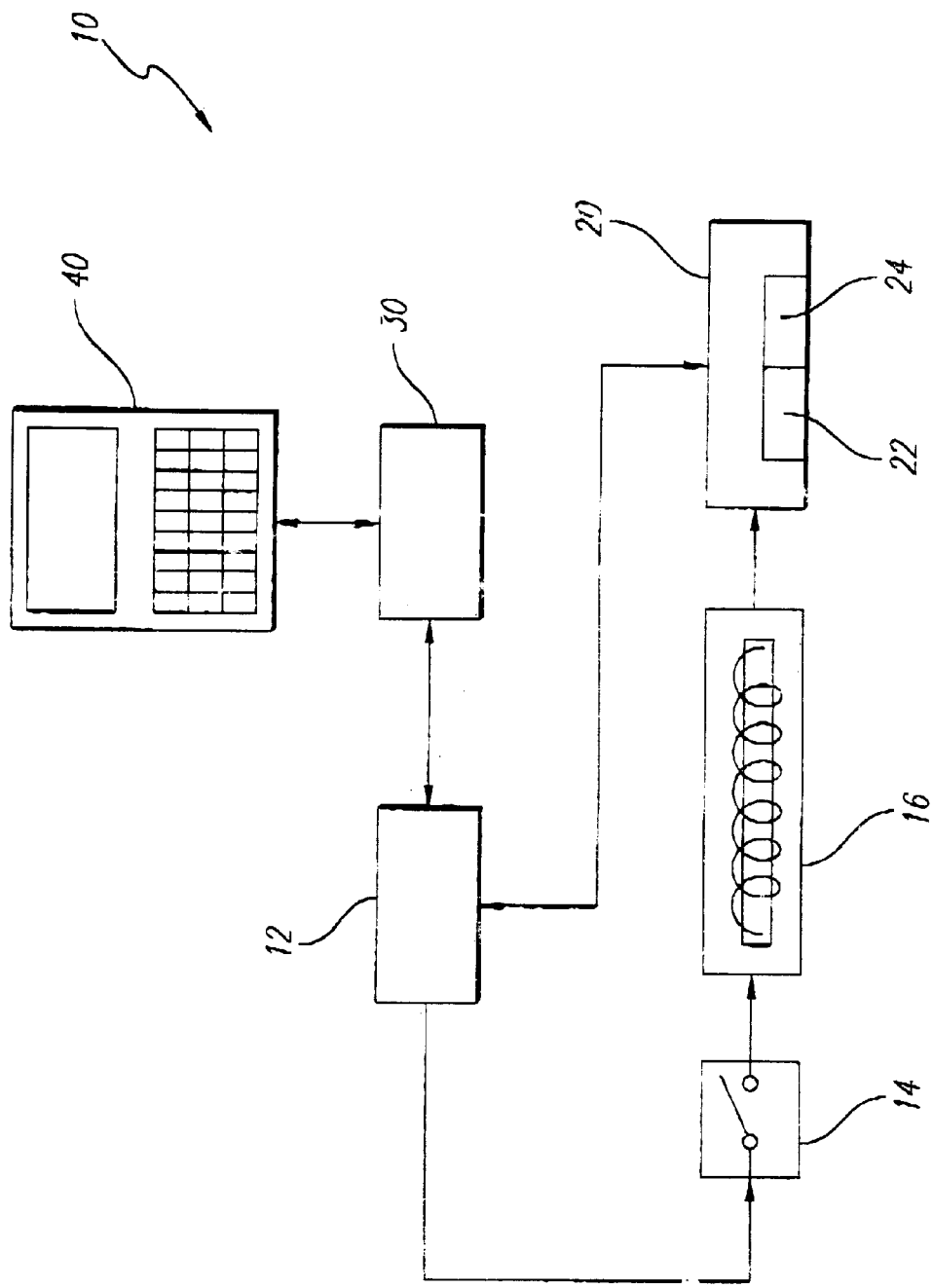
FIG. 1 is a block diagram of the infant ventilator of the present invention.

FIG. 1 discloses a block diagram of the overall system of the present invention, comprising a dual microprocessor system 10, having a first microprocessor, control micro 12, preferably a Motorola 68HC11F1 microcontroller, for controlling a switch 14 that controls a exhalation or respiratory solenoid 16 (also termed a "delivery breath" solenoid) for a electro-pneumatic, continuous flow, time cycled, pressure limited, positive-pressure ventilator 20, that delivers respiratory gas such as air and oxygen to a patient (e.g., both neonatal and pediatric patients) for external respiration. The system 10 has one or more pressure transducers, a trigger pressure transducer 22, which has high resolution and attempts to sense a patient's efforts to breathe (patients pressure differential) and a proximal pressure transducer 24, which has a lower resolution and senses a patient's proximal pressure profiles. Both pressure transducers 22, 24 are software driven and ultimately may use the same hardware to sense raw pressures, in analog format, converted to digital format with a A/D converter (ADC), as part of the system 10 for sensing the breathing pressure fed to or sensed by the patient, either at the Y-adapter of the ventilator, or at the patient's trachea. A second microprocessor, an interface micro 30 (interface microprocessor) also preferably a Motorola 68HC11F1 microcontroller, communicates with the first controller microprocessor 12, for controlling the patient information gathered by the first microprocessor 12 and displays it on a display control console 40, which is preferably an LCD screen and membrane touch screen I/O console. The present invention is concerned with the software architecture for the first microprocessor 12, the control micro 12 (control microprocessor system). Control microprocessor system 12 of the apparatus is a finite state machine that controls the solenoid to delivers a "breath" from the ventilator to the patient. The software architecture that controls the micro 12 preferably resides in RAM accessed by the control micro 12 (and optionally may be stored in PROM, EEPROM or EPROM as firmware), is in the form of a finite state machine representation. Note when the ventilator is "exhaling" respiratory gas the patient is "inhaling", and vice versa. Details concerning the second, display-oriented microprocessor 30, the console 40, and the hardware associated with the solenoid are not part of the present invention. Details concerning the respirator hardware are the subject matter of the copending and commonly assigned U.S. patent application entitled "Improved Ventilator Triggering Device," Ser. No. 09/183,761, filed on Oct. 30, 1998, incorporated by reference herein. The software for the control micro 12 is written and compiled for the high level C language, using a PC platform.

Figure 2:
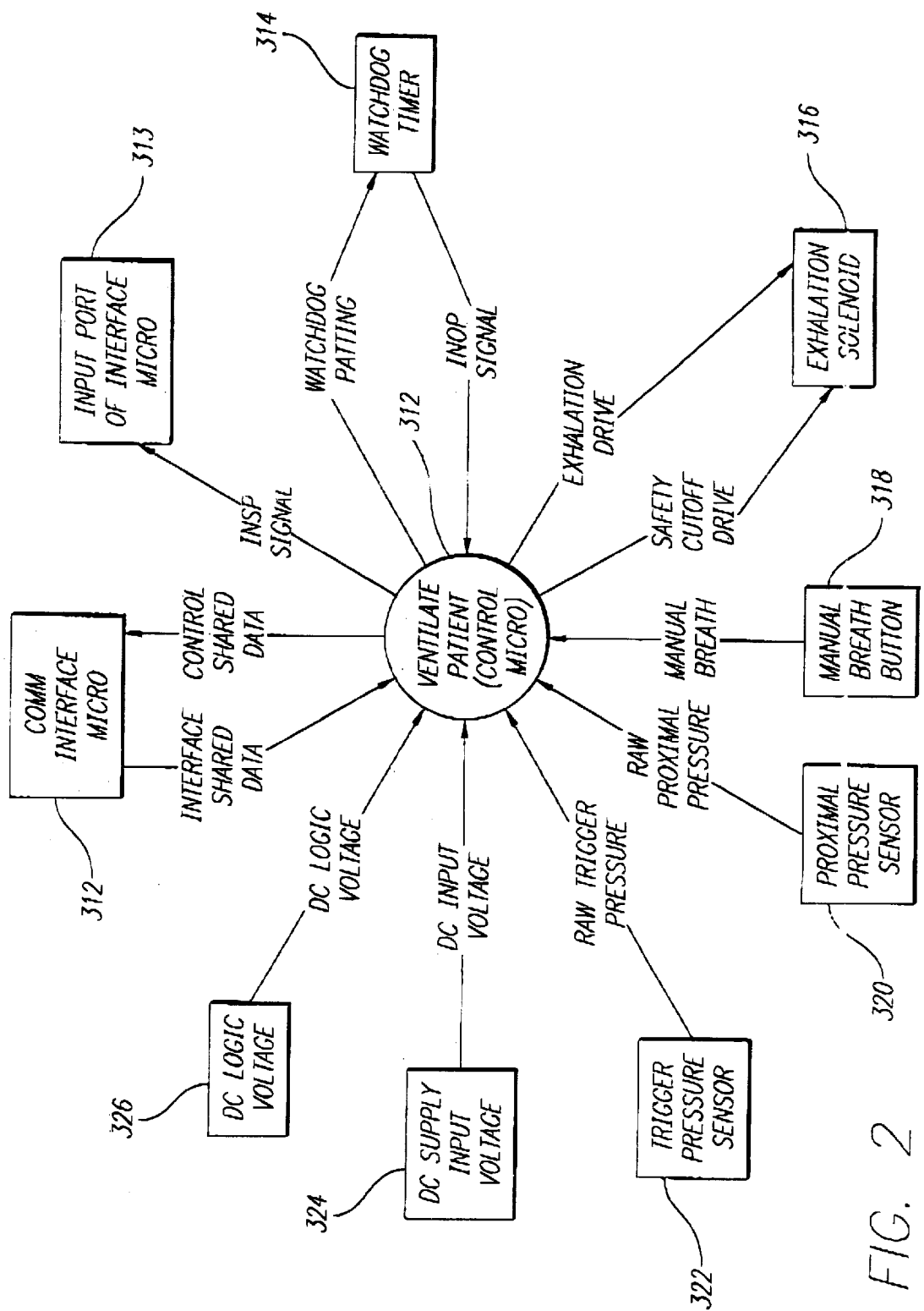
FIG. 2 is a type interaction context diagram of the ventilator system used in the present invention.

The context diagram in FIG. 2 shows the information (signals and control data) flowing between the control micro 12 of FIG. 1 and all the external entities with which it interfaces. The rectangular boxes or terminators represent the external entities; the single circle or process represents the complete control micro 12 software system. Thus, going clockwise from the top of FIG. 2, the control micro 12 interacts with the interface micro 30 via SPI data (Serial Peripheral Interface data) that indicates intercommunication 312. A INSP signal, for respiratory rate measurement signal, is processed and delivered to input port 313 of the interface micro 30. A watchdog timer 314 is monitored, with the watchdog timer periodically polled (or patted) and suitable error signal conditions (INOP signal) monitored. Next the exhalation solenoid 316 is monitored and controlled, which controls how much respiratory gas is exhaled by the machine into the patient. A manual breath button 318 controls the delivery of a single shot of respiratory gas into a patient. A proximal pressure sensor 320 measures the patient airway pressure at the ventilator, while a trigger pressure sensor 322 senses the pressure at the Y-adapter of the respirator, attempting to measure the patient's efforts only. A DC supply input voltage 324, suitably isolated, provides power to the control micro and any accessories, while a DC logic voltage 326 supplies logic voltage.

Figures 1, 3:
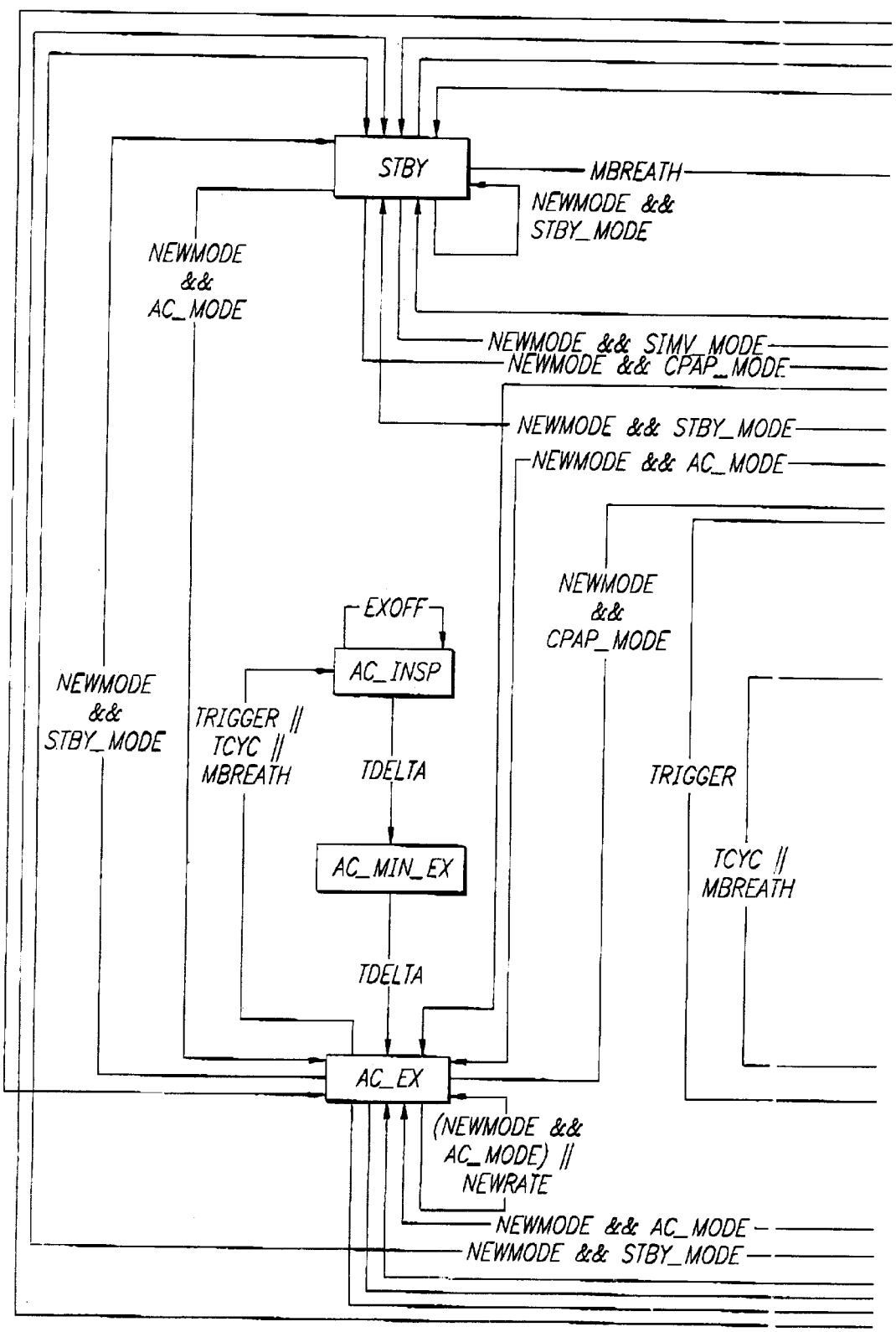
FIG. 3 (labeled over 3 sheets as FIGS. 3-1, 3-2, and 3—3) is a Mealy/Moore type finite state machine diagram of the portion of the ventilator that controls respiration that is the subject matter of this invention.
Figures 2, 3:
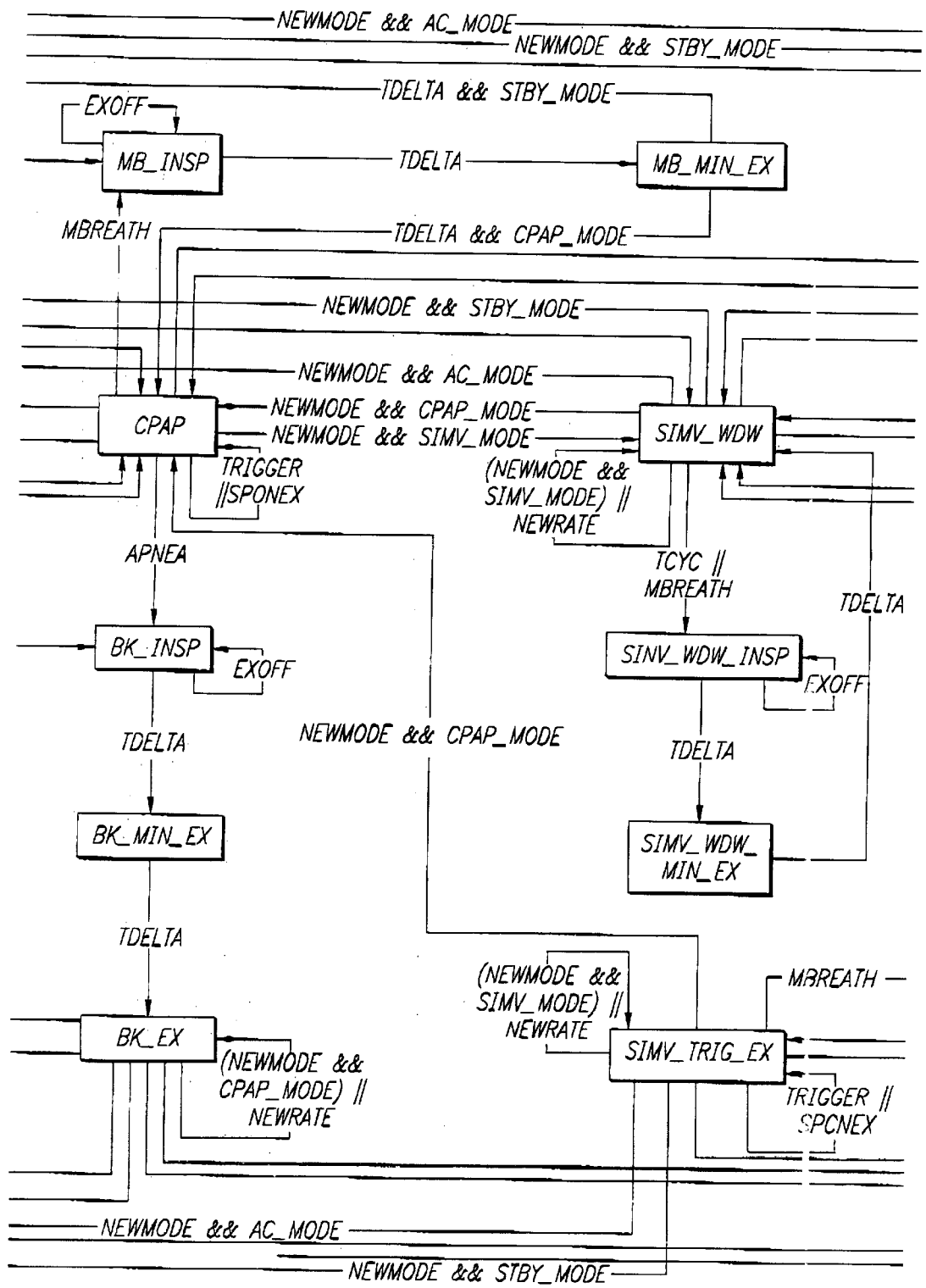
Figure 3:
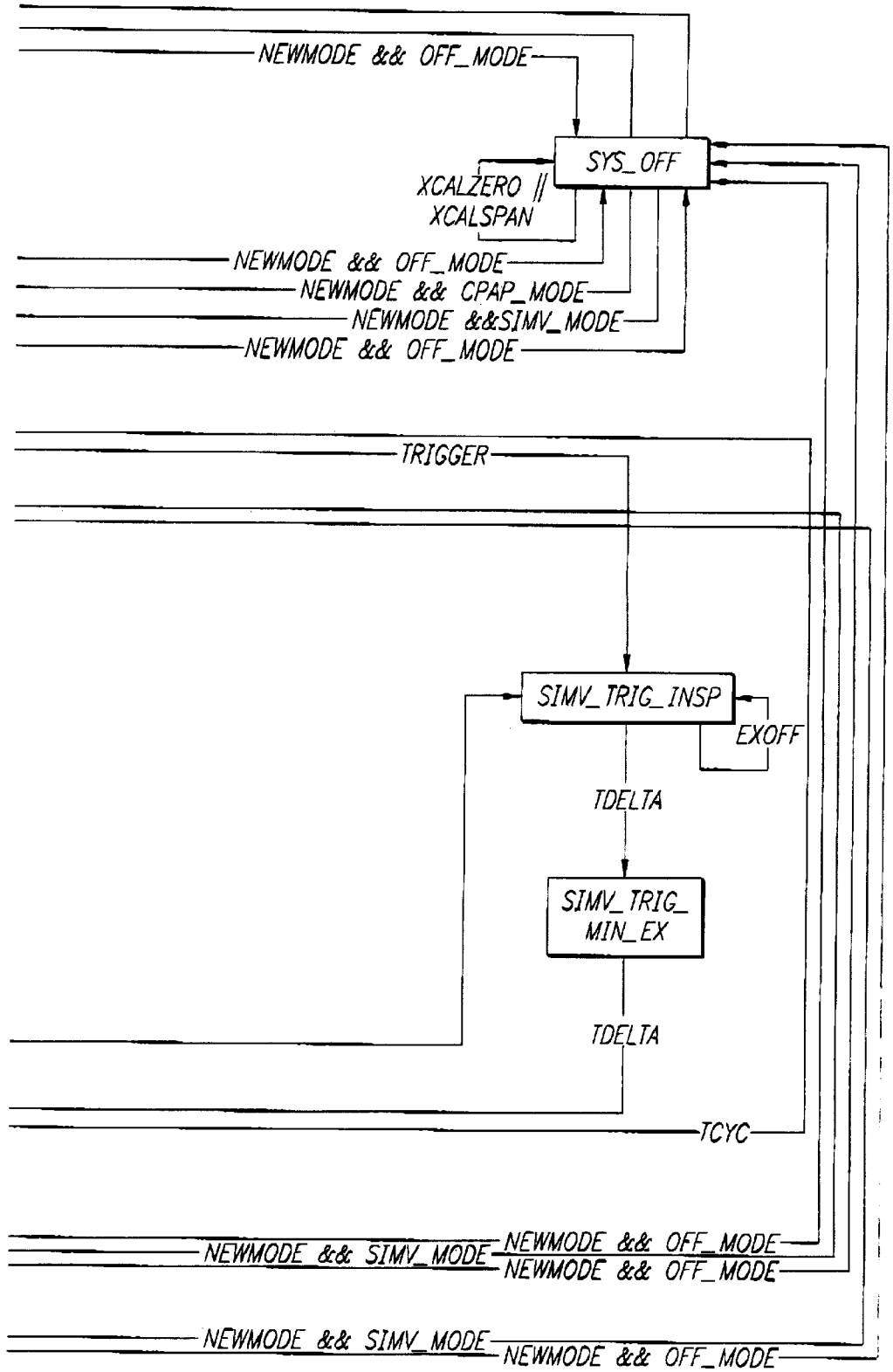

Turning attention now to FIG. 3, there is shown a Mealy/Moore type finite state machine diagram of the portion of the ventilator that controls respiration, the control micro 12. In the Mealy/Moore finite state machine diagram, the present state is indicated by alpha-numeric indicia inside the boxes, while the event or condition that causes a change in state (even if the state is to the present state) is indicated by indicia outside the box, also termed a transition, with the direction of the arrow indicating the direction of the state transition from one state to the next. Suitable actions can take place both during a transition and at any given state.

Generally speaking, and ignoring for the moment the states (modes) involved with standby mode, manual (one-shot) mode, and numerous other such modes, the operation of the control micro 12 of the respirator of the present invention can be broken down into three broad categories: a first "weaning" mode, labeled CPAP in FIG. 3, where a patient is breathing spontaneously at a positive pressure above ambient, a second "synchronous assist" ventilator mode, labeled SIMV_WDW in FIG. 3, where a patient can breathe spontaneously between synchronized assisted machine breaths, and a third conventional mechanical mode, labeled AC_EX in FIG. 3, a traditional mode of first generation ventilators, where the patient is solely machine delivered or assisted in breathing with none of the features mentioned in the other two categories.

Aside from these three general categories of operation of the ventilator, there are numerous other modes (aside from the modes within each of the three general categories described above, as explained further herein). These modes have to do with when the apparatus is in standby mode, in system off mode, and in manual mode (one-shot mode), where a single cycle of respiration is performed on the patient.

Thus, one mode of operation of the control micro 12 is the standby mode, or the STBY state (mode), where the respirator is in a state of repose. As shown graphically by the Mealy/Moore finite state machine diagram of FIG. 3, when the control micro 12 of the ventilator is in a standby mode, there can be a plurality of events and conditions that trigger a change of state for the system.

One change is for the state to transition from the STBY mode (state) to the STBY mode (i.e., the system does not change state) upon the detection of a STBY_MODE condition during a NEWMODE event, which may be a predetermined portion of the program that checks for the occurrence of a change in mode. In this case the state does nothing (i.e., system does not change state). Another change in state is from the STBY mode (state) to the AC_EX mode (state) upon the detection of a AC_MODE condition during a NEWMODE event. Such an AC_MODE condition may result from an operator depressing a button or switch on the console operator interface designating the AC_EX mode of operation, as is described further herein. The state can also change from STBY to SYS_OFF, where the system is turned off, upon detection of a OFF_MODE condition during a NEWMODE event, as indicated by the reference arrow. The condition to trigger the change of state to SYS_OFF may be input by an operator from an operator interface console. In the SYS_OFF mode all events are reinitialized, all timers are stopped (which preferably are software timers but may be hardware timers) and the ventilator has its power turned off. Any state variables referencing the system state is changed to reflect the new state, SYS_OFF, as is true during any change of state. In addition, as a safety precaution, SYS_OFF is the only state where instruments and hardware may be calibrated.

The state can also change from the STBY mode (state) to the manual breath inspiration state, the MB_INSP mode (state), upon the happening of an event designated MBREATH. This occurs when an operator pushes a button on the console designating the MBREATH mode of operation, as described herein.

The MBREATH mode of operation, designated as the state MB_INSP, is for a "one-shot" delivery of respiratory gas upon the depressing of a button on the apparatus interface console. When in the MB_INSP state the software changes state to another state MB_MIN_EX upon the detection of a TDELTA event. A TDELTA event, signifies that the inspiratory time for a patient has just elapsed, as measured by a delta timer, which preferably is software driven and is set to count a predetermined time selected by the operator, which may depend on such factors as the patients age, weight and medical condition, and the like. The apparatus is instructed by the processor to deactivate the exhalation solenoid, and re-start a delta timer with a minimum exhalation time. If, however, prior to the TDELTA event a EXOFF event is detected, the state states the same. The EXOFF event, an emergency event, exists as a safety precaution, upon the occurrence of a high inspiratory pressure from the patient or a prolonged inspiratory time, which may set off an alarm in the system, and the control micro 12 will be instructed to turn off the exhalation solenoid, and restart the delta timer with a minimum exhalation time. In the state MB_MIN_EX the apparatus simply waits for the TDELTA event timer to elapse, and upon lapsing, if the condition CPAP_MODE is sensed (e.g., such as if an operator has depressed a button on the console for putting the apparatus into the CPAP mode) then the state changes to CPAP, otherwise the state changes back to the standby mode, STBY.

Turning attention again to the STBY state, the apparatus can change from STBY mode to CPAP mode upon the detection of a CPAP_MODE condition during a NEWMODE event. Such a CPAP_MODE condition may result when an operator pushes a button on the operator interface console designating the CPAP mode of operation, as is described further herein.

A particularly popular mode of operation of the control micro 12 is the CPAP mode, or "weaning" mode, where the ventilator allows the patient to breathe spontaneously. Thus, when the trigger pressure sensor 322 detects that a patient is breathing spontaneously, the ventilator does nothing but monitor the patient. Graphically in the Mealy/Moore finite state machine diagram of FIG. 3 this is shown by arrow CPAP, which is in a present state of repose, CPAP, and which, upon the happening of a TRIGGER or SPONEX event, goes to the next state of CPAP, (e.g., maintains its present state). A TRIGGER event is signaled if the average trigger pressure crosses over an established reference pressure threshold. A SPONEX event is signaled if the average trigger pressure crosses above the average baseline pressure to indicate the start of an exhalation phase. The CPAP state also transfers information about the fact that spontaneous inhalation or exhalation has occurred to the interface micro 30, to display status about the change in state, and to reset the software to indicate that a TRIGGER or SPONEX event has been completed.

Another state transition in the CPAP "weaning" mode is shown as triggered by the event APNEA, which causes the control micro 12 of the ventilator to transition from the CPAP mode to the "backup ventilation" mode. This mode is entered whenever there is an apnea, or a temporary cessation of breathing. Upon the detection of apnea, the software transitions to another state, termed the state BK_INSP, as shown in FIG. 3. The software for the finite state machine control micro 12 calls an appropriate module that notes the change in state, starts a cyclical timer module that is loaded in "one-shot" mode (non-periodic) with appropriate data particular to the patient for what type of mechanical breath delivery is required of the exhalation solenoid of the machine, and begins the respiratory cycle of the machine (the inspiratory cycle of the patient).

At state BK_INSP, there are two events that will cause a transition in the state machine that are to be programmed: a TDELTA event and an EXOFF event. In the former, the TDELTA event, signifies that the inspiratory time for a patient has just elapsed. Thus it deactivates the exhalation solenoid 16 of the apparatus, and re-starts a delta timer with a minimum exhalation time. The next state reached is then the BK_MIN_EX state, which waits until another TDELTA event is reached, and at which point the state of the machine decays to the state BK_EX. However, the EXOFF event exists as a safety precaution, upon the occurrence of a high inspiratory pressure from the patient or a prolonged inspiratory time alarm, the control micro 12 will be instructed to turn off the exhalation solenoid, and restart the delta timer with a minimum exhalation time. Suitable alarms may be sounded by the interface micro for a nurse or physician to be summoned.

At state BK_EX a variety of new states may be entered into, depending on what events and conditions occur. For example, if event TRIGGER is detected, where the average trigger pressure crosses over the established reference pressure threshold, this signifies that the patient has attempted to breathe. Consequently, the new state entered into will be back to the "weaning" state, CPAP, as referenced by reference arrow TRIGGER in FIG. 3.

If, however, in state BK_EX, the conditions TCYC or MBREATH are sensed by the software, the state entered into is BK_INSP and the exhalation process is repeated for one more cycle, with the patient being forced air by the delivery breath solenoid. Condition TCYC is entered into if the cyclical timer for the current respiratory cycle lapses before any other condition is sensed in state BK_EX (e.g., the other arrows leading out of the state diagram box BK_EX). Condition MBREATH is sensed if a physician or nurse manually pushes a "manual aspiration" button, forcing air into a patient for one-shot (cycle) only.

Turning attention now to the AC_EX mode, there is shown another state of the apparatus for forced air delivery. The AC_EX mode of operation, for "assist/control" mode, is a more primitive, traditional form of machine aspiration than the SIMV_WDW mode described herein. In the AC_EX state, the ventilator does monitor the patient's breathing to detect a TRIGGER, but not synchronously as in the SIMV_WDW mode discussed herein, nor does the machine wean a patient who is breathing spontaneously (i.e., naturally) but may need mechanical backup assistance when he/she goes apenic (i.e., apnoeic), as in the CPAP mode discussed herein. Rather, in the AC_EX mode, the ventilator cyclically exhales respiratory gas into the patient in a regular, albeit changeable, mechanical cycle. Thus, as indicated by the Mealy/Moore finite state machine diagram of FIG. 3, the state AC_EX can change into a plurality of other states depending on what events and conditions are triggered when the software driven apparatus is in the AC_EX state.

For one, upon the occurrence of a NEWMODE event when in the AC_EX mode, which may be a predetermined portion of the program that checks for the occurrence of a change in mode, and upon the occurrence of a OFF_MODE condition received during a NEWMODE event, the program will switch (e.g., via a call to a function while in a switch statement) to the next state SYS_OFF, which will turn off the ventilator and reinitialize all pending events, as well as stop all timers and disable trigger and spontaneous breath detentions. In addition, as is true for all changes in state, a state variable may be changed to indicate a SYS_OFF mode.

Upon the occurrence of a STBY_MODE condition during a NEWMODE event when in the AC_EX state, the software changes state to the standby mode, STBY, as explained herein. Upon the occurrence of a AC_MODE condition during a NEWMODE event when in the AC_EX state, or upon the occurrence of a NEWRATE event, the software does not change state (e.g., remains in the same state). The occurrence of a AC_MODE condition may be in response to an operator pushing a button on a console. The NEWRATE event is an update of the existing respiratory cycle time. Upon the occurrence of a NEWRATE event the software also performs the following functions: (a) if the new respiratory cycle time for the AC_EX mode is less than the currently set respiratory time, and is also less than the elapsed respiratory cycle time, the timer for the current cycle time is ended and re-started with the new respiratory time; (b) if the new respiratory cycle time is less than the current respiratory time, and is also greater than the elapsed respiratory cycle time, the difference of the new and the elapsed respiratory cycle time is used to complete the current cycle time; and (c) if the new respiratory cycle time is greater than the current cycle time, no modification is needed to the current cycle timer.

Upon the occurrence of the events of either TRIGGER or MBREATH or TCYC during a NEWMODE event when in the AC_EX state, the software changes state to the new state AC_INSP, which starts the respiratory cycle. The TRIGGER event is signaled if the average trigger pressure crosses over an established reference pressure threshold. The TCYC timer is a counter timer to periodically trigger an event, such as when the current respiratory cycle is ended. The MBREATH event is initiated when an operator, e.g., a physician or nurse, pushes a button on the interface console of the respirator apparatus to trigger that a manual breath cycle be actuated, which causes the apparatus to deliver a single shot of respiratory gas into the patient every time the button is depressed.

From the state AC_INSP the apparatus may change to the AC_MIN_EX state, upon the occurrence of a TDELTA event, signifying that the inspiratory time for a patient has just elapsed, and further it may change state from the state AC_MIN_EX back to AC_EX upon the further occurrence of a TDELTA event (in effect 2 times TDELTA in time from the delta timer allows a change of state from AC_INSP to AC_EX), and complete the respiratory cycle, with no further air forced into the patient at the end of the cycle. At the state AC_INSP the occurrence of an EXOFF event (which exists as a safety precaution, upon the occurrence of a high inspiratory pressure from the patient or a prolonged inspiratory time) will cause the control micro 12 to turn off the exhalation solenoid, and restart the delta timer with a minimum exhalation time.

State AC_EX can also change state to the CPAP "weaning" mode, as discussed herein, upon the occurrence of a CPAP_MODE condition during a NEWMODE event, such as an operator pushing a button on the console to start the CPAP mode when the NEWMODE window is open. Likewise, the AC_EX state may change to the SIMV_WDW state, as further discussed herein, upon the occurrence of a condition SIMV_MODE during a NEWMODE event.

State SIMV_WDW will now be described. In this state, breathing is machine assisted in a synchronous manner, but with sophisticated feedback in the ventilator to determine when to have the machine exhale respiratory gas into the patient, based on the patient's inhalation patterns and the pressure sensed by a trigger pressure transducer. Further, upon detection of a TRIGGER event, the state of the respirator changes to allow the possibility of a change to a different mode, as discussed further herein.

Turning to FIG. 3, state SIMV_WDW changes to state SIMV_WDW_INSP when the events TCYC or MBREATH are triggered, such as when the cyclical timer TCYC lapses before any other condition is sensed in state, or when a manual mode (one-shot) button is depressed on the console by a nurse. The respirator solenoid is suitably activated to give a single shot of respiratory gas to the patient. In state SIMV_WDW_INSP the one-shot respiration process is continued. State SIMV_WDW_INSP does not change upon the happening of an EXOFF event, which is an emergency event, otherwise upon the end of a predetermined time set by software timer TDELTA, the state changes to state SIMV_WDW_MIN_EX, which is a state involved at the end of an inspiratory phase, which restarts a delta timer with the predetermined minimum exhalation time (which may be set by an operator), turns off the exhalation solenoid 16, and signals the interface micro 30 of the change and relays SPI (Serial Peripheral Interface) data to the display console concerning the state of the control micro.

State SIMV_WDW can also change to state SIMV_TRIG_INSP, upon the detection of a TRIGGER event, where a patient attempts to breathe. The state function executed from the transition from state SIMV_WDW to SIMV_TRIG_INSP turns on a TDELTA cyclical timer to a predetermined value selected by the operator, passes information to the console, and starts the solenoid to start inspiratory phase of the respiratory cycle, so that the solenoid exhales gas from the machine to the patient, synchronous with the patients own attempts to breathe. At state SIMV_TRIG_INSP, there are two events that will trigger a state change, either a EXOFF event, an emergency event as discussed above, that exists as a safety precaution to activate emergency procedures in the respirator in the event of occurrence of a high inspiratory pressure from the patient or a prolonged inspiratory time, which maintains the state, or a TDELTA event, which signifies the minimum inspiratory time has lapsed, and changes the state to SIMV_TRIG_MIN. At the state SIMV_TRIG_MIN the state changes automatically to SIMV_TRIG_EX upon the lapsing of a TDELTA time (in effect TDELTA time is one-half the actual respiratory cycle time). Upon the change of state from SIMV_TRIG_MIN to SIMV_TRIG_EX, any delta timers are stopped, the states dealing with MBREATH, TRIGGER, and SPONEX are reset to a pending state, and the state is set to check to see if any of the events or conditions in SIMV_TRIG_EX are tripped.

In state SIMV_TRIG_EX, a state function is run (typically using a switch command in a do-while loop) that checks to see if the events NEWMODE, TCYC, MBREATH, TRIGGER, NEWRATE or SPONEX have occurred, and executes the appropriate change in state, initiating the appropriate action. Thus, the NEWMODE even coupled with the condition OFF_MODE, STBY_MODE, AC_MODE, SIMV_MODE, CPAP_MODE will trigger the change in state the following states, respectively: to state SYS_OFF, where the system is turned off, as previously discussed, state STBY, where the system is in repose, state AC_EX, a mainly mechanical mode of respiration as discussed, and the state CPAP_MODE, or weaning mode, as discussed. During each of these transitions the state variables are updated to reflect the change in state and appropriate initialization steps may be taken to ensure the states are set to proper values to respond.

State SIMV_TRIG_EX may change state to three other states, as shown in FIG. 3. The state may change from SIMV_TRIG_EX to the SIMV_TRIG_INSP state, upon the happening of a MBREATH event, such as when an operator depresses a button on the console for a "single-shot" of respiration (a single respiratory cycle upon depressing of the manual breath button) in which case the state changes to accommodate one additional cycle. In addition, the state may not change, or remain the same, upon the happening of a TRIGGER event, a TCYC event or a SPONEX event. The occurrence of a TRIGGER event indicates the patient is breathing by his or her own efforts, consequently, no additional change of state is required for the time being, unless the cyclical timer TCYC has been triggered. Upon the occurrence of a TCYC event when in the state SIMV_TRIG_EX, the synchronous cycle of the SIMV_WDW mode is repeated by transformation back to the state SIMV_WDW. Condition TCYC is entered into if the cyclical timer for the current respiratory cycle lapses before any other condition is sensed in state SIMV_TRIG_EX. Finally, also while in state SIMV_TRIG_EX, the event SPONEX indicates the start of an exhalation phase of a spontaneous breath, such as the average trigger pressure crosses above the average baseline pressure.

Regarding the hardware of the control micro 12 used in the present invention, it is preferably a Motorola 68HC11F1 chip, operated as a finite state machine by the control micro software of the present invention. The section titles and overall organization of the present detailed description are for the purpose of convenience only and are not intended to limit the present invention.

Although the present invention has been described in terms of the preferred embodiments above, numerous modifications and/or additions to the above-described preferred embodiments would be readily apparent to one skilled in the art. Thus, one of ordinary skill might be able to combine two or more states where there is only one transitional event branch from one state to the next, such as states SIMV_TRIG_INSP and SIMV_TRIG_MIN_EX or AC_INSP and AC_MIN_EX, without loss of generality. It is intended that the scope of the present invention extends to all such modifications and/or additions and that the scope of the present invention is limited solely by the claims set forth below.

What is claimed is:

1. A software driven ventilator system comprising:
   a ventilator system controlled by a hardware controller, wherein said ventilator system contains a positive-pressure respirator displacing air controlled by an exhalation solenoid activated by said controller;
   said controller implemented as a finite state machine in software;
   said software implementing said finite state machine controller has a plurality of states for controlling said ventilator system, comprising:
      a first weaning state, the CPAP mode, wherein a patient is allowed to breath naturally, with the controller monitoring the patient's breathing, and activating said ventilation system, as a backup to the patient's natural breathing, in the event of apnea;
      a second Assist/Control state, the AC_EX mode, wherein a patient is forced respiratory gas by activation of said exhalation solenoid at a predetermined time cycle; and,
      a third synchronous assist state, the SIMV_WDW mode, wherein a patient is forced respiratory gas for inhalation by activation of said exhalation solenoid at a predetermined time cycle, and said controller monitoring the patient for natural breathing.

2. The invention according to claim 1, further comprising a console wherein:
   wherein each of said states may be entered into from any other state, by the selective activation of a keypad switch on said console.

3. The invention according to claim 1, further comprising:
   a standby state, the STBY mode, from which any other state may be entered;
   said software implemented controller in said STBY mode changes into a one of a plurality of other states upon the occurrence of a transition event, said plurality of states comprising the STBY mode, the CPAP mode, the AC_EX mode, and the SIMV_WDW mode.

4. The invention according to claim 3, further comprising:
   a manual breath inspiration state, the MB_INSP mode, wherein respiratory gas is forced into said patient for a single time cycle upon the selective activation of a predetermined switch.

5. The invention according to claim 4, wherein:
   said software implemented controller in said MB_INSP mode changes state to one of a plurality of other states, upon the occurrence of a transition event, said states and transition events comprising:
      said MB_INSP mode, wherein there is no change of state, upon the occurrence of a transition event indicating an emergency condition with the patient, the EXOFF event;
      a second manual inspiration state, the MB_MIN_EX mode, upon the occurrence of a transition event indicating a lapse of a predetermined time interval, the TDELTA event, wherein from said MB_MIN_EX mode said state changes to said STBY mode, upon the occurrence of a TDELTA event and upon selective activation of a predetermined switch on said console, and said MB_MIN_EX mode changes to said CPAP mode, upon the occurrence of a TDELTA event and upon selective activation of a predetermined switch on said console.

6. The invention according to claim 1, wherein said software implemented controller has a state comprising a system off state, the SYS_OFF mode, wherein said controller is calibrated in said SYS_OFF mode, and wherein said SYS_OFF mode can change to said AC_EX mode, said STBY mode, said CPAP mode and said SIMV_WDW mode upon the selective activation of a predetermined switch on said console.

7. The invention according to claim 1, wherein said software implemented controller in said CPAP mode changes states to one of a plurality of other states, upon the occurrence of a transition event, said states and transition events comprising:
   a backup inspiration state, the BK_INSP mode, wherein a patient is forced respiratory gas by activation of said exhalation solenoid, upon the occurrence of a transition event indicating the detection of apnea from the patient, the APNEA event;
   said SIMV_WDW mode, upon the occurrence of a transition event indicating the selective activation of a predetermined switch;
   said AC_EX mode, upon the occurrence of a transition event indicating the selective activation of a predetermined switch.

8. The invention according to claim 7, further comprising:
   a manual breath inspiration state, the MB_INSP mode, wherein respiratory gas is forced into a patient for a single time cycle upon the selective activation of a predetermined switch;
   said CPAP mode changes to said MB_INSP mode upon the occurrence of a transition event indicating selective activation of said predetermined switch.

9. The invention according to claim 7,
   wherein said software implemented controller in said BK_INSP mode changes states to one of a plurality of other states, upon the occurrence of a transition event, said states and transition events comprising:
      said BK_INSP mode, so there is no change of state, upon the occurrence of a transition event indicating an emergency condition with the patient, the EXOFF event;
   a second inspiration state, the BK_MIN_EX mode, upon the occurrence of a transition event indicating the lapse of a predetermined time interval, the TDELTA event.

10. The invention according to claim 9,
    wherein said software implemented controller in said BK_MIN_EX mode changes states to another state upon the occurrence of a transition event, comprising a state from which said backup inspiration state, BK_INSP, may be repeated, the BK_EX mode, upon the occurrence of said TDELTA event;
    wherein said BK_EX mode changes state to one of a plurality of different states, upon the occurrence of a transition event, comprising:
       said AC_EX, SIMV_WDW, and CPAP modes, upon the occurrence of a transition event indicating activation of a predetermined switch;
       said CPAP mode, upon the occurrence of an attempt by the patient to breath naturally, the TRIGGER event.

11. The invention according to claim 10, wherein:
    wherein said BK_EX mode changes state to one of a plurality of different states, upon the occurrence of a transition event, comprising:
       said BK_INSP mode, upon either the occurrence of a lapse of a another predetermined time interval, the TCYC event, or the activation of a predetermined switch;

said BK_EX mode, so that the state does not change, upon the occurrence of either a update of respiratory cycle time, said update reflected in said time interval TDELTA and TCYC, the NEWMODE event, or the activation of a predetermined switch.

12. The invention according to claim 1, wherein said software implemented controller in said SIMV_WDW mode changes states to one of a plurality of other states, upon the occurrence of a transition event, said states and transition events comprising:

a state where said exhalation solenoid is activated to force respiratory gas into a patient upon the detection of the occurrence of an attempt by the patient to breathe, the TRIGGER event, termed the SIMV_TRIG_INSP mode.

13. The invention according to claim 12, wherein said SIMV_TRIG_INSP state changes state to one of a plurality of other states, upon the occurrence of a transition event, said states and transition events comprising:

said SIMV_TRIG_INSP state, for no change in state, upon the occurrence of a transition even indicating an emergency condition with the patient, the EXOFF event;

a subsequent state synchronous assist state, SIMV_TRIG_MIN_EX, upon the occurrence of a lapse of a predetermined time interval, the TDELTA event.

14. The invention according to claim 12, wherein:

said software implemented controller in said SIMV_WDW mode changes states to a subsequent state that, upon the lapse of a predetermined time interval, changes state to a another subsequent state, the SIMV_TRIG_EX mode, upon which said exhalation solenoid is deactivated, and the inspiration cycle is completed;

wherein said SIMV_TRIG_EX mode may change state to one of a plurality of other states, upon the occurrence of a transition event, said states and transition events comprising:

said SIMV_WDW mode, upon the lapse of a predetermined time TCYC;

one of said CPAP mode, STBY mode, and AC_EX mode, upon the detection of the activation of a predetermined switch associated with said CPAP, STBY and AC_EX modes, said SIMV_TRIG_EX mode, for no change of state, upon the detection of an emergency condition in a patient, the SPONEX event, or upon the attempt by the patient to breath naturally, the TRIGGER event, before the lapse of said predetermined time TCYC;

said SIMV_TRIG_EX mode, for no change of state, upon the detection of the activation of a predetermined switch associated with said SIMV_TRIG_EX mode; and said SIMV_TRIG_EX mode, for no change of state, upon the detection of a new cycle time for the respiratory cycle associated with states SIMV_WDW and SIMV_TRIG_EX, a NEWRATE event.

15. The invention according to claim 1, wherein:

said software implemented controller in said AC_EX mode changes states to one of a plurality of other states, upon the occurrence of a transition event, said states and transition events comprising:

a first inspiration state, the AC_INSP mode, wherein a patient is forced respiratory gas by activation of said exhalation solenoid, upon the occurrence of at least one transition event comprising the detection of an attempt by a patient to breath naturally, the TRIGGER event, the expiration of a predetermined time, the TCYC event, and upon the occurrence of a transition event indicating the selective activation of a predetermined switch, the MBREATH event.

16. The invention according to claim 15, wherein said software implemented controller changes state from said AC_EX state to one of a plurality of different states, upon the occurrence of a transition event, comprising:

said STBY mode, said CPAP mode, said SIMV_WDW mode, and a system off state, the SYS_OFF mode, wherein said controller is calibrated in, wherein said SYS_OFF mode can change to said AC_EX mode, said STBY mode, said CPAP mode and said SIMV_WDW mode upon the selective activation of a predetermined switch on said console.

17. The invention according to claim 15, wherein:

said software implemented controller in said first inspiration state, the AC_INSP mode, changes states, upon the occurrence of a transition event, said states and transition events comprising:

a second inspiration state, the AC_MIN_EX mode, said exhalation solenoid activated to force air into a patient, upon the occurrence of the lapse of a predetermined time, the TDELTA event;

said first inspiration state, the AC_INSP mode, for no change in state, upon the occurrence of upon the occurrence of a transition event indicating an emergency condition with the patient, the EXOFF event.

18. The invention according to claim 17, wherein:

said software implemented controller in said second inspiration state, AC_MIN_EX mode, changes states to said AC_EX mode, and deactivates said respiration solenoid to complete the respiratory cycle.

19. A method of operation of a positive-pressure respirator ventilator system containing a exhalation solenoid activated by a controller implemented as a finite state machine comprising the steps of:

implementing said controller as a finite state machine;

providing a change of state to a plurality of states for said finite state machine controller for controlling the operation of said exhalation solenoid.

20. The method of operation according to claim 19, further comprising the steps of:

providing a change of state to a first state, the CPAP mode, wherein a patient is allowed to breath naturally, with the controller monitoring the patient's breathing;

activating said ventilation system exhalation solenoid while in said CPAP mode, only in the event of patient apnea, as a backup to said patient's natural breathing.

21. The method of operation according to claim 20, further comprising the steps of:

providing a change of state to a second state, the AC_EX mode;

activating said exhalation solenoid to force respiratory gas into a patient at a predetermined time cycle when in said AC_EX mode.

22. The method of operation according to claim 20, further comprising the steps of:

providing a change of state to a third state, the SIMV_WDW mode;

activating said exhalation solenoid to force respiratory gas into a patient at a predetermined time cycle when in said SIMV_WDW mode;

monitoring the patient for natural breathing during said SIMV_MODE state.

23. The method of operation according to claim 22, further comprising the steps of:
provided a change of state to a fourth state, the STBY mode, from which any of said other states may be entered;
changing states from said STBY mode to said other states upon the occurrence of a transition event.

24. The method of operation according to claim 22, further comprising the steps of:
providing a change of state to a manual breath inspiration state, the MB_INSP mode, said MB_INSP mode entered into by said controller upon the selective actuation of a predetermined switch;
forcing respiratory gas into said patient for a single time cycle upon the selective activation of said predetermined switch.

25. The method of operation according to claim 22, comprising the steps of:
providing a change of state, when in said CPAP mode, to a plurality of other states for said controller to change to upon the occurrence of a transition event, said steps comprising:
providing a change of state to a backup inspiration state, the BK_INSP mode, wherein a patient is forced respiratory gas by activation of said exhalation solenoid, upon the occurrence of a transition event indicating the detection of apnea from the patient, the APNEA event;
providing a change of state to said SIMV_WDW mode, said change of state occurring upon the selective activation of a predetermined switch;
providing a change of state to said AC_EX mode, said change of state occurring upon the selective activation of a predetermined switch.

26. The method of operation according to claim 25, further comprising the steps of:
providing a change of state to a manual breath inspiration state, the MB_INSP mode, wherein respiratory gas is forced into a patient for a single time cycle, upon the selective activation of a predetermined switch;
whereby said CPAP mode changes to said MB_INSP mode upon the selective activation of said predetermined switch.

27. The method of operation according to claim 22,
providing a change of state for said controller while in said BK_INSP mode, to change states to one of a plurality of other states, upon the occurrence of a transition event, comprising the steps of:
changing to said BK_INSP mode, so there is no change of state, upon the occurrence of a transition event indicating an emergency condition with the patient, the EXOFF event;
changing to a second inspiration state, the BK_MIN_EX mode, upon the occurrence of a transition event indicating the lapse of a predetermined time interval, the TDELTA event.

28. The method of operation according to claim 27, further comprising the steps of:
providing a change of state for said controller in said BK_MIN_EX mode to change states to another state upon the occurrence of a transition event, comprising a state from which said backup inspiration state, BK_INSP, may be repeated, the BK_EX mode, upon the occurrence of said TDELTA event;
providing a change of state for said BK_EX mode to change state to one of a plurality of different states, upon the occurrence of a transition event, comprising the steps of:
changing to said AC_EX, SIMV_WDW, and CPAP modes, upon the occurrence of a transition event indicating activation of a predetermined switch;
changing to said CPAP mode, upon the occurrence of an attempt by the patient to breath naturally, the TRIGGER event.

29. The method of operation according to claim 28, wherein:
wherein said BK_EX mode changes state to one of a plurality of different states, upon the occurrence of a transition event, comprising:
changing to said BK_INSP mode, upon either the occurrence of a lapse of a another predetermined time interval, the TCYC event, or the activation of a predetermined switch;
changing to said BK_EX mode, so that the state does not change, upon the occurrence of either a update of respiratory cycle time, said update reflected in said time interval TDELTA and TCYC, the NEWMODE event, or the activation of a predetermined switch.

30. The method of operation according to claim 22, comprising the steps of:
providing a change of state, when in said SIMV_WDW mode, to a plurality of different states, upon the occurrence of transition events, comprising:
changing to a state where said exhalation solenoid is activated to force respiratory gas into a patient upon the detection of the occurrence of an attempt by the patient to breathe, the TRIGGER event, termed the SIMV_TRIG_INSP mode.

31. The method of operation according to claim 30, wherein said SIMV_TRIG_INSP state changes state to one of a plurality of other states, upon the occurrence of a transition event, comprising the steps of:
changing to said SIMV_TRIG_INSP state, for no change in state, upon the occurrence of a transition event indicating an emergency condition with the patient, the EXOFF event;
changing to a subsequent state synchronous assist state, SIMV_TRIG_MIN_EX, upon the occurrence of a lapse of a predetermined time interval, the TDELTA event.

32. The method of operation according to claim 30, further comprising the steps of:
providing for a change in state for said software implemented controller in said SIMV_WDW mode to a subsequent state that, upon the lapse of a predetermined time interval, changes state to a another subsequent state, the SIMV_TRIG_EX mode, upon which said exhalation solenoid is deactivated, and the inspiration cycle is completed;
wherein said SIMV_TRIG_EX mode may change state to one of a plurality of other states, upon the occurrence of a transition event, said states and transition events comprising the steps of:
changing state to said SIMV_WDW mode, upon the lapse of a predetermined time TCYC;
changing state to one of said CPAP mode, STBY mode, and AC_EX mode, upon the detection of the activation of a predetermined switch associated with said CPAP, STBY and AC_EX modes;
changing state to said SIMV_TRIG_EX mode, for no change of state, upon the detection of an emergency condition in a patient, the SPONEX event, or upon the attempt by the patient to breathe spontaneously, the TRIGGER event, before the lapse of said predetermined time TCYC;

changing state to said SIMV_TRIG_EX mode, for no change of state, upon the detection of the activation of a predetermined switch associated with said SIMV_TRIG_EX mode; and changing state to said SIMV_TRIG_EX mode, for no change of state, upon the detection of a new cycle time for the respiratory cycle associated with states SIMV_WDW and SIMV_TRIG_EX, a NEWRATE transition event.

33. The method of operation according to claim 33, wherein:

said software implemented controller in said AC_EX mode changes states to one of a plurality of other states, upon the occurrence of a transition event, comprising the steps of:

changing state to a first inspiration state, the AC_INSP mode, wherein a patient is forced respiratory gas by activation of said exhalation solenoid, upon the occurrence of at least one transition event comprising the detection of an attempt by a patient to breathe, the TRIGGER event, the expiration of a predetermined time, the TCYC event, and upon the occurrence of a transition event indicating the selective activation of a predetermined switch, the MBREATH event.

34. The method of operation according to claim 33, wherein said controller changes state from said AC_EX state to one of a plurality of different states, upon the occurrence of a transition event, comprising the steps of:

changing state to said STBY mode, said CPAP mode, said SIMV_WDW mode, and a system off state, the SYS_OFF mode, wherein said controller is calibrated in, wherein said SYS_OFF mode can change to said AC_EX mode, said STBY mode, said CPAP mode and said SIMV_WDW mode upon the selective activation of a predetermined switch on said console.

35. The method of operation according to claim 33, wherein:

said software implemented controller in said first inspiration state, the AC_INSP mode, changes states, upon the occurrence of a transition event, comprising the steps of:

changing state to a second inspiration state, the AC_MIN_EX mode, said exhalation solenoid activated to force air into a patient, upon the occurrence of the lapse of a predetermined time, the TDELTA event;

changing state to said first inspiration state, the AC_INSP mode, for no change in state, upon the occurrence of upon the occurrence of a transition event indicating an emergency condition with the patient, the EXOFF event.

36. The method of operation according to claim 35, further comprising the steps of:

said controller in said second inspiration state, AC_MIN_EX mode, changes states to said AC_EX mode, and deactivates said respiration solenoid to complete the respiratory cycle.

* * * * *